United States Patent [19]

Millar

[11] Patent Number: 4,771,782

[45] Date of Patent: Sep. 20, 1988

[54] METHOD AND ASSEMBLY FOR INTRODUCING MULTIPLE CATHETERS INTO A BIOLOGICAL VESSEL

[75] Inventor: Huntly D. Millar, Houston, Tex.

[73] Assignee: Millar Instruments, Inc., Houston, Tex.

[21] Appl. No.: 931,273

[22] Filed: Nov. 14, 1986

[51] Int. Cl.$^4$ .............................................. A61B 5/00
[52] U.S. Cl. .................... 128/637; 128/673; 128/675; 128/748
[58] Field of Search ............... 128/637, 642, 672, 673, 128/675, 748

[56] References Cited

U.S. PATENT DOCUMENTS 3,038,465 6/1962 Allard et al. ......................... 128/675
4,456,013 6/1984 De Rossi et al. .................... 128/675

OTHER PUBLICATIONS

Product brochure of Schneider Medintag AG, entitled: "Monorail-Bonzel Coronary Dilation System".

*Primary Examiner*—Kyle L. Howell
*Assistant Examiner*—Randy Citrin
*Attorney, Agent, or Firm*—Arnold, White & Durkee

[57] ABSTRACT

A method and assembly for inserting a plurality of sensors into a biological fluid vessel for diagnosing the condition of the vessel or fluid. A pressure sensor is described which is particularly adapted for use with a steerable guidewire for selective positioning in the vessel. In one use, the method is used in coronary diagnosis, to determine the pressure gradient across a coronary valve or stenosis in the coronary arterial tree. In this method, a guiding catheter is percutaneously inserted with its distal end proximate the ostium. A guidewire is inserted through the guiding catheter and subselectively positioned in a region of interest in the coronary arterial tree. Multiple pressure sensors are then threaded down the guidewire and positioned in the region of interest. Advantageously, such pressure sensors are approximately 3 French in diameter, allowing multiple sensors to be threaded through the guiding catheter and positioned in the small arteries of the coronary arterial tree. Such pressure sensors can be used in conjunction with other sensors (e.g. temperature, pH, or Doppler sensors) and are useful in a variety of applications (e.g. venous, urinary tract, esophageal).

17 Claims, 2 Drawing Sheets

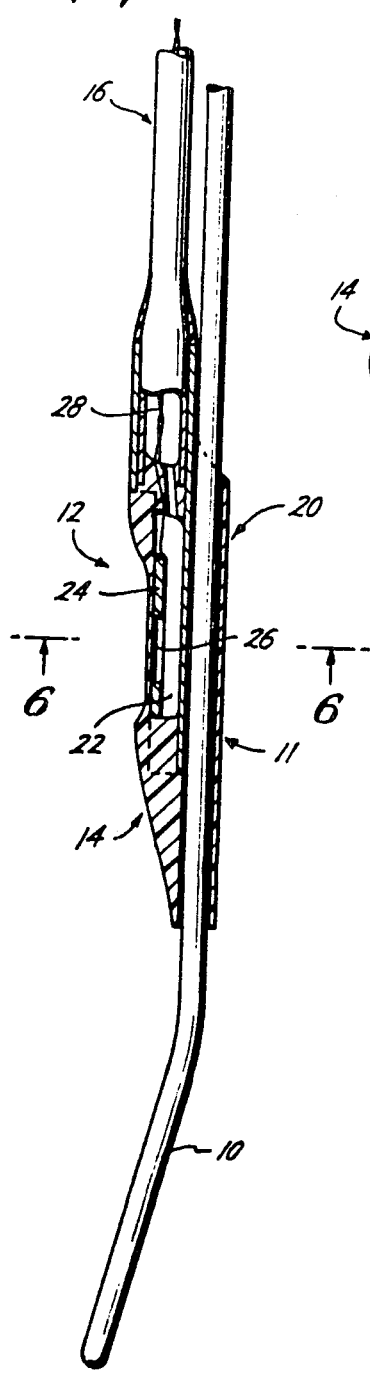
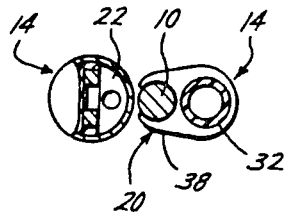
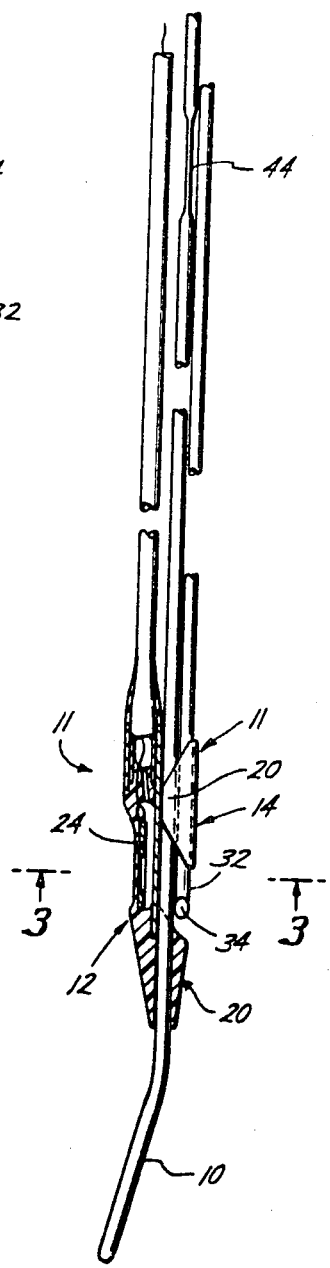

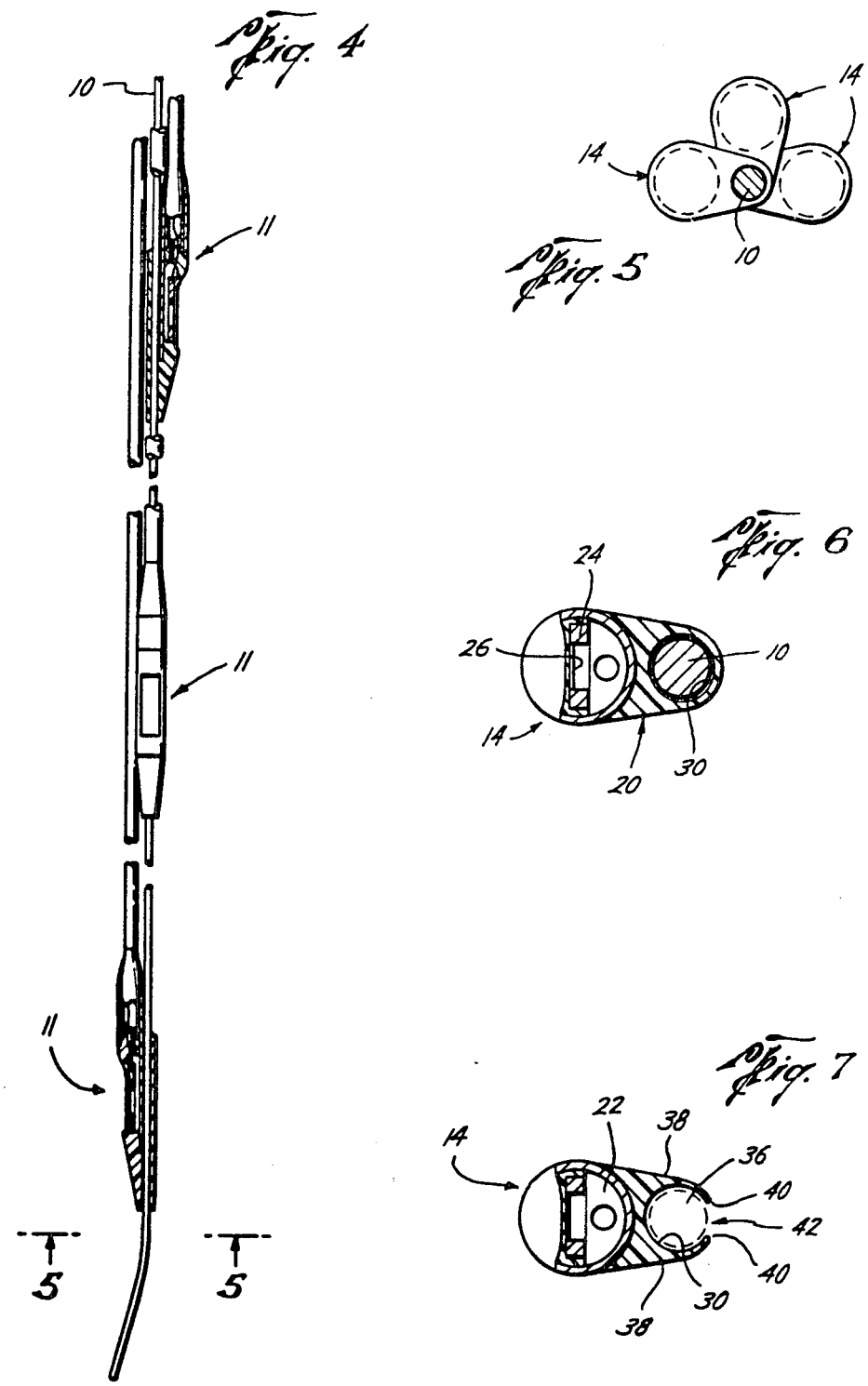

METHOD AND ASSEMBLY FOR INTRODUCING MULTIPLE CATHETERS INTO A BIOLOGICAL VESSEL

BACKGROUND OF THE INVENTION

1. Field of the Invention

This invention relates to a method and assembly for inserting a plurality of catheters in vivo in a biological vessel, such as a blood vessel, urethra, or the like. In particular, the method and assembly of the present invention contemplates a single, steerable guidewire inserted into a vessel, and one or more sensor-carrying catheters engaging the guidewire which are independently inserted into the vessel in a building block fashion.

2. Description of the Relevant Art

In the past few years, there has been a sharp increase in the number of diagnostic and therapeutic procedures performed in vivo in fluid carrying biological vessels. For example, since the work of Grunzig in the late 1970's, coronary angioplasty has become a common therapeutic procedure for dilating a region of stenosis (i.e. constriction) in the coronary arteries. Coronary angioplasty is, in many cases, preferable treatment over such alternatives as open heart bypass surgery. In recent years, valvuloplasty has become an acceptable procedure for treating aortic stenosis across a heart valve.

Of course, there are a wide variety of therapeutic procedures for treating various aspects of heart disease in vivo which avoid open heart surgery. Further, diagnostic techniques, such as angiography, have become increasingly sophisticated and reliable in predicting the location and nature of heart disease. A typical angiolocation plasty procedure usually involves a number of discrete diagnostic and therapeutic steps.

Particular problems associated with invasive diagnostic and therapeutic cardiac catheterization techniques include size restrictions of such invasive devices, and also the ability to measure a variety of fluid characteristics. For example, pulmonary artery pressures are conventionally monitored using a flow directed catheter (e.g. Swan-Ganz catheter, see U.S. Pat. No. 3,995,623, incorporated herein by reference) which carries a pressure sensing lumen through the right ventricle into the pulmonary artery. Such right heart analysis is somewhat simplified in that Swan-Ganz catheters typically have an external diameter of about 7 French (2.3 mm), and are easily flow directed to the region of interest in the right heart.

Left heart coronary catheterization is somewhat more difficult in that any diagnostic (i.e. sensor) or therapeutic device cannot be flow directed, but must be advanced against the direction of blood flow either by direct manipulation of the catheter or by advancing it over a steerable guidewire. Conventional therapeutic and diagnostic catheter-mounted devices include a tubular catheter body having an internal lumen throughout its entire length for receiving the guidewire. U.S. Pat. Nos. 4,195,637 and 4,545,390 (incorporated herein by reference) discuss catheters and guidewires. Advancement of conventional, catheter-mounted therapeutic or diagnostic devices along a guidewire around the aortic arch to the branch points of the left and right coronary ostium is not unduly complex, and such conventional catheter-mounted devices can be sized on the order of 6 French. However, for such devices to be subselectively positionable past the coronary ostium requires an external diameter on the order of 3 French (1 mm) and an easily manipulable guidewire. The coronary arterial tree past the ostium is a prime region of interest both for diagnostic and therapeutic (e.g. angioplasty) procedures.

Difficulties with such conventional guidewire-catheters having receiving lumens include: steerability of the guidewire, visualization of the coronary arteries and stenosis, and exchangeability of catheters. Exchangeability of such catheters is a particular problem (e.g. exchanging a conventional angioplasty catheter for an infusion catheter or larger angioplasty catheter) in that the distal tip of the guidewire must be maintained in the selected coronary artery while the exchange takes place. This exchange is typically accomplished using an exchange guidewire having a length (approximately 3 meters) over twice the length of the catheter so that a portion of the exchange guidewire can be held secured while the catheter is slipped over the end of the guidewire.

A major difficulty with such conventional catheters is the practical inability to carry multiple sensors, or a combination of sensors and therapeutic devices. For example, it would be preferable to avoid the necessity of exchange of conventional catheters, which might be accomplished if the catheter carried the desired variety of sensors and therapeutic devices. Such a catheter might include an angioplasty dilating balloon, an infusion lumen, a pressure sensor, a pH sensor, a temperature sensor, a fluid velocity-determining sensor, or any combination thereof. Such a complex catheter which would incorporate a wide variety of sensors and therapeutic devices would be expensive and perhaps oversized. For wide spread use, it is preferable that any invasive catheter be disposable to avoid the painstaking task of cleaning the guidewire receiving lumen or any infusing lumen which is exposed to the blood or other biological fluid. Thus, such a complex multiple device catheter would preferably either be disposable or easily cleaned, and would be sized on the order of 3–4 French external diameter.

Though the heart is a primary anatomical area of interest, other anatomical regions are particularly appropriate for use of such conventional guidewire-receiving catheters for therapeutic and diagnostic use. For example, such conventional catheters are often used in the digestive tract for treating and investigating stomach disorders. Such probe-carrying catheters might be intubated in the alimentary canal over a guidewire into the small intestine. Such probes might include balloon catheters, perfusion catheters, pH and myoelectric probes, or pressure sensors.

Another common invasive use of such guidewire-receiving catheters involves insertion of such catheters into the urinary tract. For example, a catheter carrying several pressure transducers or pressure lumens might be inserted transurethrally into the bladder and slowly withdrawn out of the urethra to determine a urethral pressure profile. As with the coronary catheters discussed above, the size of such catheters is a major restriction and the expense of such multiple sensor catheters is often prohibitive.

SUMMARY OF THE INVENTION

The problems outlined above are in large measure solved by the method and structures contemplated by the present invention. While the catheters discussed above contemplate a single catheter having a guidewire-receiving lumen and perhaps one or more diagnostic or therapeutic devices, the present invention contemplates a plurality of catheters each having a coupling structure adapted for engaging a single guidewire. That is, while conventional catheters contemplate a long lumen (e.g. 150 cm.) for slidably engaging the guidewire, the present invention contemplates a relatively short coupling structure (e.g 1 cm) for slidably engaging the guidewire.

Because the catheter of the present invention does not include a guidewire-receiving lumen, the catheter body itself can be relatively small (e.g. less than 2 French, 0.7 mm). Preferably, the distal end of the catheter of the present invention is coupled to an elongated body carrying the diagnostic or therapeutic device. The coupling structure depends from the device-carrying body and the greatest diameter of the body and coupling structure is on the order of 3-4 French. This arrangement not only allows a plurality of device-carrying catheters to be coupled to a common guidewire, but also presents a completed assembly which is still on the order of 3-4 French maximum diameter. It will be appreciated that the present invention involves a building-block approach in which a variety of sensors, probes, infusion catheters, and other diagnostic or therapeutic devices can be inserted in the vessel and selectively removed without disturbing the position of the guidewire in the vessel.

The method of the present invention broadly comprises first inserting the guidewire into the vessel with the distal end of the guidewire positioned in the region of the vessel of interest. A first device is connected to the guidewire and broadly includes a body, an elongated catheter connected to the body, and a coupling structure depending from the body which is adapted for engaging the guidewire. Such a device might comprise a diagnostic pressure sensor. A second device might simply be an infusion lumen in which the body and coupling structure act merely to engage the catheter to the guidewire and to position the distal opening of the lumen in the region of interest. In most cases, the present invention contemplates that the device comprises a diagnostic tool such as a pressure sensor, temperature sensor, pH sensor, or velocity sensor.

After connecting the first device to the guidewire, the first device is inserted into the region of the vessel of interest with the coupling structure slidably engaging the guidewire. The catheter trails the body into the vessel and is generally longitudinally aligned and juxtaposed relative to the guidewire. In the method of the present invention, a second device is connected to the guidewire and inserted into the vessel region in a fashion similar to the first device. The first and second devices are positioned along the guidewire in the region of interest with the respective catheters radially spaced about the guidewire.

In many applications, such as cardiac catheterization, a guiding catheter having a working lumen is first inserted into the vessel. The guidewire is then inserted through the guiding catheter into the vessel and positioned in the region of interest, with the first and second devices sequentially engaged to the guidewire and inserted through the guiding catheter into the vessel. Even though a typical cardiac catheterization guiding catheter is on the order of 8-9 French, the assembly comprising the guidewire and first and second devices is still easily threaded through the guiding catheter and positionable in the desired region.

The assembly of the present invention includes an elongated, flexible, steerable guidewire adapted for insertion into the vessel and having a distal end positionable in the region of interest. The assembly preferably includes a pressure sensor and another device, each having an elongated body, a longitudinal passage in the body for slidably receiving the guidewire, and an elongated catheter coupled to the body in longitudinal alignment therewith. The pressure sensor includes a cavity in the body which is isolated from the biological fluid when the sensor is inserted in the vessel, and a lumen in the catheter in communication with the cavity. A transducer is mounted to the body of the sensor for measuring the pressure differential between the biological fluid and the pressure within the cavity when the sensor is inserted in the vessel. The pressure sensor and other device are both adapted for sliding reception on the guidewire for positioning in the region of the vessel of interest, with the respective catheters radially spaced about the guidewire.

In one preferred form, the invention contemplates a system for introducing one or more diagnostic or therapeutic devices into the biological vessel, it being understood that a simple infusion lumen might also comprise such a device. In this embodiment, the diagnostic or therapeutic device is connected to an elongated body, and an elongated catheter is connected to the body in longitudinal alignment. A coupling mechanism depends from the body and is adapted for slidably engaging a guidewire, such that with the guidewire positioned in a biological vessel and the coupling mechanism engaging the guidewire, the body is slidable along the length of the guidewire in the vessel.

In one embodiment, the coupling mechanism includes a pair of parallel fingers depending from the body and defining a guidewire-receiving groove between the fingers. The distal ends of each finger are curled towards one another to define a slot having a dimension less than the diameter of the distal section of the guidewire. Thus, the dimension of the slot prevents disengagement of the coupling mechanism from at least the distal section of the guidewire preventing inadvertent disengagement of the body from the guidewire while in the vessel.

In this embodiment, the system may include an elongated, flexible, steerable guidewire having a constricted fitting region which is outside the vessel with the guidewire positioned in the vessel. The fitting region has a transverse diameter less than the slot dimension between the fingers to facilitate engagement and disengagement of the coupling mechanism to the guidewire. As an alternative to the fitting region, the fingers of the coupling mechanism may comprise a flexible, resilient material such that the distal ends of the fingers can be spread apart and the guidewire inserted through the slot into the guidewire receiving groove.

BRIEF DESCRIPTION OF THE DRAWINGS

FIG. 1 is a fragmentary, elevational view of a guidewire and device in accordance with the present invention, in which the device is in partial section depicting a pressure sensor embodiment;

FIG. 2 is a fragmentary, elevational view in partial section in which the coupling structure of a first device (a pressure sensor) and a second device (an infusion lumen) are cooperatively configured to position the pressure sensor transducer and distal end of the infusion lumen in the same general location in the vessel;

FIG. 3 is a vertical sectional view taken along lines 3—3 of FIG. 2;

FIG. 4 is an elevational, fragmentary, view in partial section of an assembly in accordance with the present invention showing three devices;

FIG. 5 is a vertical sectional view taken along line 5—5 of FIG. 4;

FIG. 6 is a vertical sectional view taken along line 6—6 of FIG. 1; and

FIG. 7 is a vertical sectional view of an alternative embodiment similar to the embodiment of FIG. 6 in which the guidewire-receiving passage through the body comprises a groove.

DESCRIPTION OF THE PREFERRED EMBODIMENTS

Turning now to the drawings, an elongated, flexible guidewire 10 is shown which is insertable into a biological vessel. In FIG. 1, the guidewire is particularly adapted for cardiac catheterization and is approximately 0.014 inches (0.3 mm) in outer diameter. In the drawing (FIG. 4), a plurality of diagnostic devices 11 are shown coupled to the guidewire 10. In FIG. 1, a single device 11 comprising a pressure sensor 12 is shown which is similar to Applicant's prior application Ser. No. 912,195, which is incorporated herein by reference.

Broadly speaking, each device 11 includes an elongated body 14, and elongated catheter 16 coupled to the body 14 in longitudinal alignment therewith and coupling mechanism 20 depending from the body 14.

In more detail, the body 14 of the pressure sensor 12 includes an internal cavity 22 which is isolated from the biological fluid with the sensor 12 immersed in the fluid. An elongated, rectangular pressure member 24 is mounted along one wall of the body 14 and includes a thin, flexible diaphragm 26. With the sensor 12 inserted into biological fluid the diaphragm 26 is flexed in response to the pressure of the fluid. In most cases, the cavity 22 is simply filled with ambient air so that the diaphragm 26 deforms in response to differential pressure between the biological fluid pressure and ambient air pressure. Strain gauges (not shown) are coupled across the diaphragm and are responsive to the flexure of the diaphragm 26. Electrical leads 28 are coupled to the strain gauges and lead through the catheter to an external electronic processing device.

Viewing FIGS. 1 and 6, the coupling mechanism 20 depends from the body 14 and defines an elongated passage 30 for slidably receiving the guidewire 10 as shown in FIG. 1. The diameter of the passage 30 is approximately 0.016 inches so that the guidewire 10 is easily slidable therethrough. Overall, the largest dimension of the body 14 and coupling mechanism 20 (the vertical dimension as depicted in FIG. 6) is approximately 3-4 French or slightly in excess of 1 mm.

Turning to FIGS. 2-5 and 7, a variety of alternatives and modifications are illustrated, the same numerals being applied for the structures illustrated in FIGS. 2-5 and 7 as applied to the embodiment illustrated in FIGS. 1 and 6. In FIG. 2 a guidewire 10 is illustrated in which two different devices 11 are mounted. For illustrative purposes, the first device comprises a pres sensor 12 similar to the pressure sensor 12 illustrated in FIG. 1. The second device in FIG. 2 comprises an infusion catheter 32 which provides a working lumen having a distal opening 34.

The pressure sensor 12 has been modified in FIG. 2 in that the coupling mechanism 20 is truncated and located to depend from the distal end of the body 14. As can be seen in FIG. 2, the coupling mechanism 20 of the infusion catheter 32 is located such that the distal opening of the lumen 34 is located in the same general axial location (transverse plane of the biological vessel) as the sensor member 24 of the pressure sensor 12. It will be appreciated that two or more devices 11 may have their coupling mechanisms 20 spaced relative to their sensor portions (e.g. sensor member 24), such that the devices 11 may be positioned with the sensors in the same general transverse cross-section in the biological vessel. For example, a first pressure sensor 12 may have its coupling mechanism 20 located at its distal end (as shown in FIG. 2), a second pressure sensor 12 may have its coupling mechanism 20 located in a medial location, while a third pressure sensor 12 may have a coupling mechanism 20 located in a proximal position on the body 14. The location of the coupling mechanisms 20 on their respective pressure sensors 12 permit the pressure sensors 12 to be all positioned on the guidewire 10 such that the three pressure sensor members 24 are in the same general location (transverse cross-section) in the vessel.

As shown more clearly in FIG. 3, the coupling mechanism 20 of the infusion catheter 32 is an alternative embodiment in which the passage 30 is not a cylindrical bore as shown in FIG. 6, but instead comprises a groove 36 as shown with more clarity in FIG. 7. As can be seen from FIG. 7, the alternative embodiment of the coupling mechanism 20 comprises a pair of depending fingers 38 which define therebetween a guidewire receiving groove 36. The distal tips 40 of the fingers 38 curl back towards one another to define a slot 42 therebetween. As can be appreciated from FIG. 7, the dimension of the slot 42 defined between the distal tips 40 is less than the outer diameter of the wire guide 10. In FIG. 7, the fingers 38 comprise a flexible, resilient material such that the tips 40 can be spread apart for receiving the guidewire 10.

FIG. 2 illustrates a variation of the guidewire 10 in that a constricted fitting region 44 is illustrated. In the embodiment of FIG. 2, the guidewire 10 includes a distal section which is designed for insertion into the vessel, and a proximal section which is intended to remain outside of the body during normal use. The fitting region 44 is located in the proximal section and preferably simply comprises a constricted, cylindrical portion of the guidewire 10 having a reduced diameter. Preferably, the diameter is approximately the dimension of the slot 42 to facilitate engagement of the coupling mechanism 20 to the guidewire 10. In an alternative form, the fitting region 44 simply comprises two parallel, flat regions on opposing sides of the guidewire 10, with the distance between the flat regions approximately the dimension of the slot 42. In FIG. 3, the fingers 38 are not necessarily flexible, and are preferably not spread apart so that coupling to the guidewire 10 can only occur in fitting region 44.

Turning to FIGS. 4 and 5, an assembly is illustrated in which three devices 11 are slidably mounted to the guidewire 10. In FIG. 4, each device 11 comprises a pressure sensor 12 identical to the pressure sensor 12 illustrated in FIG. 1. As can be perhaps best seen in FIG. 5, the pressure sensors 12 are radially mounted about the guidewire 10. Of course, the respective catheter 16 of each sensor 12 trails the respective body 14 with each catheter 16 generally longitudinally aligned and juxtaposed adjacent the guidewire 10. As can be seen in FIG. 4, in this embodiment the devices 11 are longitudinally spaced along the guidewire 10 and would be useful, for example, in determining a pressure gradient along a longitudinal region of the vessel.

Operation

Broadly speaking, the method of the present invention contemplates analyzing in vivo a biological fluid in a region of a biological fluid-carrying vessel. As an example, a hypothetical coronary angioplasty procedure will be described in which the stenosed coronary artery is located in the arterial tree past the left coronary ostium. Broadly speaking, such an angioplasty procedure might involve inserting a guiding catheter (7-8 French Sheath) through the femoral artery approach as is well known in the art. Preferably, the guidewire is advanced to a region close to the root of the ascending aortic arch. As the guidewire is advanced, several devices 11 are coupled to the guidewire 10 to assist in advancement and visualization of the position of the guidewire 10. The first device 11 may comprise a angioplasty dilating balloon in combination with a velocity-determining sensor, similar to that described in U.S. Pat. No. 4,665,925 (incorporated herein by reference). Alternatively, the guidewire 10 itself might include a velocity-determining sensor such as described in Applicant's co-pending application Ser. No. 081,308 (incorporated here in by reference). In this example, the first device 11 would include an angioplasty balloon mounted to the body 14 with the pneumatic lumen running through the catheter 16. A Doppler crystal would be fitted to the distal end of the body 14 with the electrical leads running through the catheter 16. As can be appreciated from the drawing, the streamline, low profile configuration of the body 14 aides in manipulating the device 11 past constrictions in the approach.

A second device 11 would, in this example, comprise an infusion catheter 32 as illustrated in FIG. 2 which could be used for injecting contrast medium for positioning of the guidewire 10 and devices 11 as they are advanced. Additionally, the infusion catheter 32 could be used for transcatheter pressure readings as desired. Finally, a third device 11 comprising a pressure sensor 12 would be advanced which, in most cases, would be helpful in positioning the guidewire 10 and devices 11. Other devices 11, such as pH or temperature probes, might similarly be mounted to the guidewire 10 and advanced perhaps through the aortic arch.

Eventually, the guidewire 10 is advanced to intubate the left coronary ostium using a conventional method such as the Judkins technique. The distal tip of the guidewire 10 is then manipulated and steered into the coronary artery of interest, with the stenosis identified using a variety of techniques, such as the arteriogram, fluid velocity measurements, and perhaps fluid pressure measurements. With the guidewire 10 positioned in the region of stenosis, the angioplasty balloon can be inflated to distend the stenosis and the efficacy of the treatment analyzed using one or more of the devices 11.

Assuming, that one of the devices 11 initially advanced towards the coronary arteries is to be replaced, such exchange of devices 11 is easily accomplished in accordance with the method of the present invention. For example, the first or distal device 11 and guidewire 10 are left in position in the region of the coronary artery of interest and the second device 11 is to be exchanged. The second and subsequent devices 11 can be withdrawn and once outside the body are easily slid from the guidewire 10.

In the alternative embodiments of FIGS. 2, 3, and 7, exchange is even easier. For example, the third and successive devices 11 are slid along the guidewire 10 proximal to the fitting region 44 and the second device 11 slid into the fitting region 44 and easily disengaged from the guidewire 10. Of course, if the coupling mechanism 20 comprises flexible resilient fingers 38 (FIG. 7), then a fitting region 44 is not necessary for decoupling the device 11. With the third and successive devices 11 spaced from the body (or proximal to the fitting region 44) a substitute second device 11 is easily coupled to the guidewire 10 ahead of the third and successive devices 11 and reinserted along the guidewire 10 into the fluid-carrying vessel. As can be appreciated, such exchange of devices 11 is clinically advantageous in terms of speed and maintaining position of the guidewire 10 in the diseased region of the coronary artery.

Of course, many other uses of the method and assembly of the present invention are contemplated. For example, valvuloplasty has become a common procedure for treating stenosis across a heart valve. In such a procedure, the guidewire 10 is advanced into the ventricle with a pressure sensor 12 advanced into the ventricle. A second device 11, comprising an angioplasty balloon catheter, is advanced over the guidewire 10 and positioned in the region of the heart valve. Subsequently, another pressure sensor 12 might be advanced behind the balloon catheter. In this procedure, the balloon is expanded and the aortic valve distended to relieve the stenosis.

Another application involves the use of such an assembly in accordance with the present invention in the diagnosis and perhaps treatment of urinary tract abnormalities. For example, urinary incontinence might be diagnosed with the guidewire 10 advanced through the urethra into the bladder and a first pressure sensor 12 advanced along the guidewire 10 into the bladder. A second pressure sensor 12 might then be advanced along the guidewire 10 into the urethra and bladder pressure and urethra pressure monitored. Other devices 11 might similarly be advanced for monitoring temperature, pH or velocity of the urine.

Still another application might involve diagnosis of acidity and peristaltic action of the digestive tract. In such diagnosis, the guidewire 10 would be advanced past the esophageal valve and the distal end positioned in the stomach. A first device 11, comprising a pH sensor and perhaps a pressure sensor 12 is advanced through the valve into the stomach to monitor the acidity and pressure in the stomach. A second pressure sensor 12 is then inserted into the esophageal tract above the esophageal valve. Thus, the two pressure sensors could monitor the efficacy of the esophageal valve.

As can be appreciated from the above discussion, sensors such as pressure sensors, velocity measuring sensors, pH and temperature probes, etc. can be expensive. Under current technology, all such sensors or therapeutic devices must be incorporated into a single catheter which can be very expensive. In most cases, it is necessary that such a catheter have a working lumen to allow access to the fluid vessel for injecting contrast media, monitoring pressure, or to perform similar functions. Such a working lumen is, of course, contaminated with the blood or other biological fluid and must be thoroughly cleaned if the multiple device catheter is to be reused. In view of the contamination and difficulty in cleaning, there is a strong bias towards disposable catheters. However, such a multiple sensor catheter is very expensive and not readily amenable to manufacturing as a disposable item. Oftentimes if such a multiple sensor catheter is produced, the sensors are manufactured in such a fashion to reduce cost, but offer a low fidelity instrument.

Using the method and assembly of the present invention, a favorable alternative exists. That is, the expensive devices 11 such as the sensors, can be high fidelity instruments designed for reuse. In such a situation, the infusion catheter 32 would be a low cost disposable item in view of the difficulty of adequately and efficiently cleaning the lumen of the infusion catheter 32. In the assembly of the present invention, the lumen of the catheter 16 is isolated from the fluid, so that only the external surfaces of the catheter 16 and body 14 must be cleaned—a relatively simple task. The relatively short passage 30 of the coupling mechanism 20 is readily cleaned, and in the alternative embodiment (FIGS. 2, 3, 7) comprising the groove 36, is especially easily cleaned for reuse. Thus, the high fidelity sensor-type devices 11 can be designed for reuse and the high cost of such devices 11 amortized over a number of procedures and a number of patients.

As can be appreciated from the above discussion, the method, pressure sensor, assembly and system of the present invention presents a marked practical advance over conventional catheterization methods in more efficiently diagnosing and treating in vivo.

I claim:

1. A pressure sensor adapted for engaging a steerable guidewire, comprising:
    an elongated body;
    transducer means mounted to the body
        for cooperatively defining with the body an interior cavity, the cavity being isolated from the exterior biological fluid proximate the transducer means with the sensor inserted in a biological vessel, and
        for measuring, with the sensor inserted in the fluid of a biological vessel, the pressure differential between the biological fluid proximate to the transducer and the fluid pressure within the cavity;
    a tubular catheter coupled to the body and having a lumen;
    lead means coupled to the transducer means and having a portion disposed within the lumen; and
    an elongated coupling structure depending from the body, extending less than or equal to the length of the body and longitudinally aligned therewith, the structure having a longitudinally oriented passage for slidably receiving the guidewire.

2. A pressure sensor in accordance with claim 1, the passage comprising an elongated bore.

3. A pressure sensor in accordance with claim 1, the passage comprising a groove defined between a pair of flexible, resilient fingers which are curled towards each other at its distal tips.

4. A pressure sensor in accordance with claim 1, the maximum diameter of the body and coupling structure being less than about 2 mm.

5. A pressure sensor in accordance with claim 4, the diameter of the catheter being less than about 2 mm.

6. An assembly for meauring in vivo the fluid characteristics in a region of biological fluid-carrying vessel, comprising:
    an elongated, flexible, steerable guidewire adapted for insertion in the vessel and having a distal end positionable in the region;
    a first pressure sensor device adapted for engaging the guidewire and positionable in the region, the pressure sensor including
        an elongated body having a cavity isolated from the biological fluid with the sensor inserted in the vessel;
        structure means connected to the body defining a passage longitudinally oriented with the body for slidably receiving the guidewire,
        an elongated catheter coupled to the body in longitudinal alignment therewith and defining a lumen in communication with the cavity,
        transducer means mounted to the body for measuring, with the sensor inserted in the vessel, the pressure differential between the biological fluid proximate the transducer means and the pressure within the cavity;
    a second device adapted for engaging the guidewire and positionable in the region, the device including
        an elongated body,
        structure means connected to the body defining a passage longitudinally oriented with the body for slidably receiving the guidewire,
        an elongated catheter coupled to the body in longitudinal alignment therewith,
    the first and second devices being adapted for reception on the guidewire in the region of the vessel with the respective catheters spaced about the guidewire.

7. The assembly according to claim 6, each passage comprising an elongated bore in the body.

8. The assembly according to claim 6, each passage comprising a guidewire-receiving groove defined by a pair of spaced-apart fingers.

9. The assembly according to claim 6, the guidewire having a constricted fitting region outside the vessel with the distal end positioned in the region.

10. The assembly according to claim 6, the second device including a sensor coupled to the body, the passage-defining structure of the first and seocnd device being complementarily positioned relative to the respective body for positioning the transducer means and sensor in the same general transverse cross-section of the vessel.

11. A method of positioning multiple devices in a region of biological fluid-carrying vessel, comprising the steps of:
    inserting an elongated, flexible guidewire into the vessel with the distal end of the guidewire extending into the region;
    connecting to the guidewire a first device having a body, an elongated catheter connected to the body, and a coupling structure depending from the body which is adapted for engaging the guidewire;
    inserting the first device into the vessel region with the coupling structure slidably engaging the guidewire and the catheter generally longitudinally aligned and juxtaposed relative to the guidewire;
    connecting to the guidewire a second device having a body, an elongated catheter connected to the body, and a coupling structure depending from the body which is adapted for engaging the guidewire;

inserting the second device into the vessel region with the coupling structure slidably engaging the guidewire and the catheter generally longitudinally aligned and juxtaposed relative to the guidewire, positioning the first and second devices along the guidewire with their respective bodies in the region and with the first and second catheters spaced about the guidewire.

12. The method according to claim 11, the first and second devices having cooperative coupling structure, said positioning step including positioning the first and second bodies in generally the same transverse cross-section of the vessel.

13. The method according to claim 11, said positioning step including spacing the first and second devices radially around the guidewire and longitudinally along the guidewire in the region.

14. The method according to claim 11, including the steps of:

withdrawing the second device from the vessel while maintaining the position of the guidewire and first device within the vessel;

disconnecting the second device from the guidewire while maintaining the position of the guidewire and first device within the vessel; and connected a third device to the guidewire and inserting the third device into the vessel while maintaining the position of the guidewire and first device within the vessel.

15. The method according to claim 14, the coupling structure of the second device comprising a pair of spaced-apart fingers defining an elongated, guidewire-receiving grove, the disconnecting step including the substep of shifting the guidewire from the groove in a direction transverse to the longitudinal axis of the grove.

16. The method according to claim 11, including the steps of:

providing a guidewire having a constricted fitting region located outside the vessel with the distal end of the guidewire extending into the region;

providing a second device with a coupling structure comprising a pair of spaced-apart fingers defining a guidewire-receiving groove, connecting the guidewire to the second device by shifting the fitting region between the fingers into the groove.

17. The method according to claim 16, the fingers comprising a generally inflexible material, including the step of inserting the second device into the vessel along the guidewire past the fitting region to effect slidable, locking engagement of the fingers about the guidewire.

* * * * *

UNITED STATES PATENT AND TRADEMARK OFFICE
CERTIFICATE OF CORRECTION

PATENT NO. : 4,771,782

DATED : September 20, 1988

INVENTOR(S) : Huntly D. Millar

It is certified that error appears in the above-identified patent and that said Letters Patent is hereby corrected as shown below:

In Column 1, lines 34-35, please delete "angiolocation plasty" and insert therefor -- angioplasty --.

In Column 5, line 66, please delete "pres" and insert therefor -- pressure --.

In Column 10, line 3, please delete "meauring" and insert therefor -- measuring --.

Signed and Sealed this

Third Day of October, 1989

Attest:

DONALD J. QUIGG

Attesting Officer

Commissioner of Patents and Trademarks